United States Patent
Green et al.

(10) Patent No.: US 9,222,928 B2
(45) Date of Patent: Dec. 29, 2015

(54) BIPHENOL ETHER COMPOUNDS AS MARKERS FOR LIQUID HYDROCARBONS AND OTHER FUELS AND OILS

(75) Inventors: George D. Green, Cary, IL (US); Raymond J. Swedo, Mount Prospect, IL (US)

(73) Assignee: Dow Global Technologies LLC, Midland, MI (US)

( * ) Notice: Subject to any disclaimer, the term of this patent is extended or adjusted under 35 U.S.C. 154(b) by 156 days.

(21) Appl. No.: 14/129,467

(22) PCT Filed: Jun. 28, 2012

(86) PCT No.: PCT/US2012/044616
§ 371 (c)(1),
(2), (4) Date: Dec. 26, 2013

(87) PCT Pub. No.: WO2013/003573
PCT Pub. Date: Jan. 3, 2013

(65) Prior Publication Data
US 2014/0134746 A1    May 15, 2014

Related U.S. Application Data

(60) Provisional application No. 61/502,974, filed on Jun. 30, 2011.

(51) Int. Cl.
G01N 37/00 (2006.01)
G01N 33/22 (2006.01)
C10L 1/00 (2006.01)
C10L 1/185 (2006.01)
C10M 171/00 (2006.01)
G01N 33/28 (2006.01)

(52) U.S. Cl.
CPC ............ *G01N 33/22* (2013.01); *C10L 1/003* (2013.01); *C10L 1/1852* (2013.01); *C10M 171/007* (2013.01); *C10L 2200/0423* (2013.01); *C10L 2200/0469* (2013.01); *C10L 2200/0476* (2013.01); *C10L 2230/16* (2013.01); *C10M 2207/04* (2013.01); *G01N 33/2882* (2013.01); *Y10T 436/20* (2015.01)

(58) Field of Classification Search
None
See application file for complete search history.

(56) References Cited

U.S. PATENT DOCUMENTS 5,981,283 A    11/1999 Anderson, II et al.
7,858,373 B2   12/2010 Banavali et al.
2005/0019939 A1*  1/2005 Spall et al. ............... 436/139

FOREIGN PATENT DOCUMENTS

| EP | 512404 A1 | 11/1992 |
|---|---|---|
| GB | 2382080 A | 5/2003 |
| WO | 2012154646 A1 | 11/2012 |
| WO | 2012154668 A1 | 11/2012 |
| WO | 2013/003538 A1 | 1/2013 |

OTHER PUBLICATIONS

Gilman, et al., "Dibenzofuran. XIX. Derivatives of 2,2'-Dihydroxybiphenyl", Chem. Lab. Iowa St., vol. 62, pp. 1963-1967(1940).
Sorrell, et al., "3,3'-Disubstituted 2,2'-Biphenols: Synthesis of Nonplanar, Tetradentate Chelating Ligands", J. Org. Chem., vol. 50, No. 26, pp. 5765-5769 (1985).
Sarker, et al., "Synthesis and Luminescent Studies of Poly(phenylenevinylene)s Containing a Biphenyl Moiety", Macromolecules, vol. 35, pp. 223-230 (2002).
Koloziuk, et al., "An Easy and Efficient Access to Bis-Allyloxy-Arenes", Synthetic Communications, vol. 30, No. 21, pp. 3955-3961 (2000).
Massah, et al., "Solvent-Free Williamson Synthesis: An Efficient, Simple, and Convenient Method for Chemoselective Etherification of Phenols and Bisphenols", Synthetic Communications, vol. 37 No. 11, pp. 1807-1815 (2007).
Hohnholz, et al., "Synthesis and studies on luminescent biphenyl compounds", Synthetic Metals, vol. 110, pp. 141-152 (2000).
Inoue, et al., "Simple and Efficient TiC14-Mediated Synthesis of Biaryls via Arylmagnesium Compounds", Tetrahedron, vol. 56, pp. 9601-9605 (2000).

* cited by examiner

*Primary Examiner* — Robert Xu
(74) *Attorney, Agent, or Firm* — Kenneth Crimaldi

(57) ABSTRACT

A method for marking a petroleum hydrocarbon or a liquid biologically derived fuel by adding to the petroleum hydrocarbon or liquid biologically derived fuel at least one compound having formula (I),

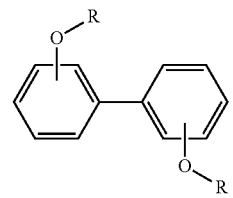

(I)

wherein R represents $C_1$-$C_{18}$ alkyl, $C_3$-$C_{18}$ alkenyl or $C_3$-$C_{18}$ alkynyl.

7 Claims, No Drawings

BIPHENOL ETHER COMPOUNDS AS MARKERS FOR LIQUID HYDROCARBONS AND OTHER FUELS AND OILS

This invention relates to a method for marking liquid hydrocarbons and other fuels and oils with suitable compounds.

Marking of petroleum hydrocarbons and other fuels and oils with various kinds of chemical markers is well known in the art. A variety of compounds have been used for this purpose, as well as numerous techniques for detection of the markers, e.g., absorption spectroscopy and mass spectrometry. For example, U.S. Pat. No. 7,858,373 discloses the use of a variety of organic compounds for use in marking liquid hydrocarbons and other fuels and oils. However, there is always a need for additional marker compounds for these products. Combinations of markers can be used as digital marking systems, with the ratios of amounts forming a code for the marked product. Additional compounds useful as fuel and lubricant markers would be desirable to maximize the available codes. The problem addressed by this invention is to find additional markers useful for marking liquid hydrocarbons and other fuels and oils.

STATEMENT OF INVENTION

The present invention provides a method for marking a petroleum hydrocarbon or a liquid biologically derived fuel; said method comprising adding to said petroleum hydrocarbon or liquid biologically derived fuel at least one compound having formula (I),

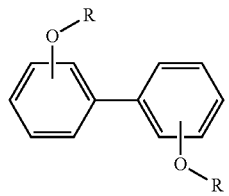

(I)

wherein R represents $C_1$-$C_{18}$ alkyl, $C_3$-$C_{18}$ alkenyl or $C_3$-$C_{18}$ alkynyl.

DETAILED DESCRIPTION

Percentages are weight percentages (wt %) and temperatures are in ° C., unless specified otherwise. Concentrations are expressed either in parts per million ("ppm") calculated on a weight/weight basis, or on a weight/volume basis (mg/L); preferably on a weight/volume basis. The term "petroleum hydrocarbon" refers to products having a predominantly hydrocarbon composition, although they may contain minor amounts of oxygen, nitrogen, sulfur or phosphorus; petroleum hydrocarbons include crude oils as well as products derived from petroleum refining processes; they include, for example, crude oil, lubricating oil, hydraulic fluid, brake fluid, gasoline, diesel fuel, kerosene, jet fuel and heating oil. Marker compounds of this invention can be added to a petroleum hydrocarbon or a liquid biologically derived fuel; examples of the latter are biodiesel fuel, ethanol, butanol, ethyl tert-butyl ether or mixtures thereof. A substance is considered a liquid if it is in the liquid state at 20° C. A biodiesel fuel is a biologically derived fuel containing a mixture of fatty acid alkyl esters, especially methyl esters. Biodiesel fuel typically is produced by transesterification of either virgin or recycled vegetable oils, although animal fats may also be used. An ethanol fuel is any fuel containing ethanol, in pure form, or mixed with petroleum hydrocarbons, e.g., "gasohol." An "alkyl" group is a substituted or unsubstituted hydrocarbyl group having from one to eighteen carbon atoms which may be in a linear, branched or cyclic arrangement, or a combination thereof. An "alkenyl" or "alkynyl" group is an alkyl group containing one or more double or triple bonds, respectively. Substitution on alkyl groups of one or more hydroxy or alkoxy groups is permitted. Preferably, alkyl groups are unsubstituted. Preferably, alkyl groups are acyclic. Preferably, the compounds of this invention contain elements in their naturally occurring isotopic proportions.

Preferably, R represents $C_1$-$C_{18}$ alkyl or $C_3$-$C_{18}$ alkenyl, preferably $C_2$-$C_{18}$ alkyl or $C_3$-$C_{18}$ alkenyl, preferably $C_1$-$C_{18}$ alkyl, preferably $C_3$-$C_{16}$ alkyl or $C_3$-$C_{16}$ alkenyl, preferably $C_2$-$C_{18}$ alkyl, preferably $C_4$-$C_{16}$ alkyl or $C_4$-$C_{16}$ alkenyl, preferably $C_4$-$C_{16}$ alkyl, preferably $C_5$-$C_{16}$ alkyl, preferably $C_8$-$C_{14}$ alkyl. In formula (I), the —OR groups can be in any position on the benzene rings, preferably in the same position on each ring (e.g., 2,2'- or 4,4'-substitution), preferably, the —OR groups are in the 2,2'-positions on the benzene rings, i.e., the compounds of formula (I) have the following structure:

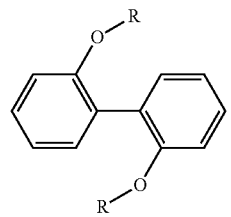

In the method of this invention, preferably the minimum amount of each marker is at least 0.01 ppm, preferably at least 0.02 ppm, preferably at least 0.05 ppm, preferably at least 0.1 ppm, preferably at least 0.2 ppm. Preferably, the maximum amount of each marker is 50 ppm, preferably 20 ppm, preferably 15 ppm, preferably 10 ppm, preferably 5 ppm, preferably 2 ppm, preferably 1 ppm, preferably 0.5 ppm. Preferably, the maximum total amount of marker compounds is 100 ppm, preferably 70 ppm, preferably 50 ppm, preferably 30 ppm, preferably 20 ppm, preferably 15 ppm, preferably 12 ppm, preferably 10 ppm, preferably 8 ppm, preferably 6 ppm, preferably 4 ppm, preferably 3 ppm, preferably 2 ppm, preferably 1 ppm. Preferably, a marker compound is not detectible by visual means in the marked petroleum hydrocarbon or liquid biologically derived fuel, i.e., it is not possible to determine by unaided visual observation of color or other characteristics that it contains a marker compound. Preferably, a marker compound is one that does not occur normally in the petroleum hydrocarbon or liquid biologically derived fuel to which it is added, either as a constituent of the petroleum hydrocarbon or liquid biologically derived fuel itself, or as an additive used therein.

Preferably, the marker compounds have a log P value of at least 3, where P is the 1-octanol/water partition coefficient. Preferably, the marker compounds have a log P of at least 4, preferably at least 5. Log P values which have not been experimentally determined and reported in the literature can be estimated using the method disclosed in Meylan, W. M & Howard, P. H., J. Pharm. Sci., vol. 84, pp. 83-92 (1995). Preferably the petroleum hydrocarbon or liquid biologically derived fuel is a petroleum hydrocarbon, biodiesel fuel or ethanol fuel; preferably a petroleum hydrocarbon or biodiesel fuel; preferably a petroleum hydrocarbon; preferably crude oil, gasoline, diesel fuel, kerosene, jet fuel or heating oil; preferably gasoline.

Preferably, the marker compounds are detected by at least partially separating them from constituents of the petroleum hydrocarbon or liquid biologically derived fuel using a chromatographic technique, e.g., gas chromatography, liquid chromatography, thin-layer chromatography, paper chromatography, adsorption chromatography, affinity chromatography, capillary electrophoresis, ion exchange and molecular exclusion chromatography. Chromatography is followed by at least one of: (i) mass spectral analysis, and (ii) FTIR. Identities of the marker compounds preferably are determined by mass spectral analysis. Preferably, mass spectral analysis is used to detect the marker compounds in the petroleum hydrocarbon or liquid biologically derived fuel without performing any separation. Alternatively, marker compounds may be concentrated prior to analysis, e.g., by distilling some of the more volatile components of a petroleum hydrocarbon or liquid biologically derived fuel.

Preferably, more than one marker compound is present. Use of multiple marker compounds facilitates incorporation into the petroleum hydrocarbon or liquid biologically derived fuel of coded information that may be used to identify the origin and other characteristics of the petroleum hydrocarbon or liquid biologically derived fuel. The code comprises the identities and relative amounts, e.g., fixed integer ratios, of the marker compounds. One, two, three or more marker compounds may be used to form the code. Marker compounds according to this invention may be combined with markers of other types, e.g., markers detected by absorption spectrometry, including those disclosed in U.S. Pat. No. 6,811,575; U.S. Pat. App. Pub. No. 2004/0250469 and EP App. Pub. No. 1,479,749. Marker compounds are placed in the petroleum hydrocarbon or liquid biologically derived fuel directly, or alternatively, placed in an additives package containing other compounds, e.g., antiwear additives for lubricants, detergents for gasoline, etc., and the additives package is added to the petroleum hydrocarbon or liquid biologically derived fuel.

The compounds of this invention may be prepared by methods known in the art. For example, alkyl halides may react with biphenols in the presence of base according to the following equation

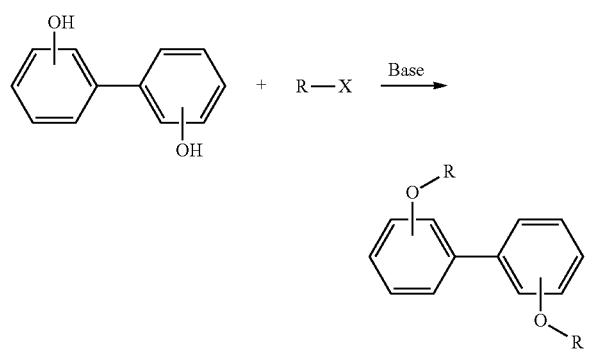

EXAMPLES

The synthesis of biphenol ethers is illustrated by the following example:

2,2'-Bis(dodecyloxy)-1,1'-biphenyl:

A 100 mL 3-neck flask was equipped with a magnetic stirrer, a reflux condenser with nitrogen blanket, and a heating mantle with a temperature controller and a thermocouple. The flask was charged with 3.74 grams (0.02 moles) of 2,2'-biphenol, 2.8 grams (0.04 moles, 85 wt. %) of potassium hydroxide, and with 25 mL of dimethylsulfoxide. The mixture was stirred under nitrogen while heating to 100° C. After about 2½ hours, the potassium hydroxide had dissolved, and the mixture was cooled to about 70° C. Dodecyl bromide (9.60 mL; d 1.038; 9.97 grams; 0.04 moles) was added in one portion. An exotherm to about 86° C. was observed. After the exotherm subsided, the reaction mixture was stirred at 70° C. After about 5 hours, the reaction mixture was poured into about 400 mL of water. The white solids that separated were collected by filtration, and were washed on the filter with several portions of water. The solids were first air-dried, and then were dried in a vacuum oven at 50° C. for about 2 hours. The yield of product was 9.49 grams (91%), having a melting point of 33-35° C. The structure was confirmed by IR, $^1$H- and $^{13}$C-NMR, and GC/MS analyses.

In those cases in which, upon quenching the reaction mixture in water, the product separated out as an oil, extraction with ethyl ether was used in place of filtration.

2,2'-Biphenol Ethers Prepared:

| R | % Yield | MP, ° C. |
|---|---|---|
| n-$C_8H_{17}$ (BOct-BBPh) | 94 | (oil) |
| n-$C_{10}H_{21}$ (BDec-BBPh) | 97 | (oil) |
| n-$C_{12}H_{25}$ (BDD-BBPh) | 91 | 33-35 |
| n-$C_{14}H_{29}$ (BTD-BBPh) | 94 | 33-35 |

GC Performance of Biphenol Ethers

Detection was done using FID (flame ionization detector).

GC Parameter Comparison:

| Parameters Column | Varian VF1701 | Agilent DB 35 |
|---|---|---|
| Maximum Temp (C.) | 300 | 360 |
| Length (m) | 30 | 15 |
| Flow Rate (ml/min) | 0.9 | 1.5 |
| Initial Temp (C.) | 100 | 100 |
| Hold (min) | 3 | 0 |
| Rate1 (C/min) | 10 | 20 |
| Final Temp1 (C.) | 290 | 280 |
| Hold (min) | 20 | 10 |
| Rate 2 (C/min) | | 20 |
| Final Temp2 (C.) | | 340 |

| | Column | |
|---|---|---|
| | Varian VF1701 | Agilent DB 35 |
| Compound | Retention Time, Min. | |
| BOct-BBPh | 9.3 | 22.1 |
| BDec-BBPh | 11.6 | 25.8 |
| BDD-BBPh | 16.8 | 33.8 |

The invention claimed is:
1. A method for marking a petroleum hydrocarbon or a liquid biologically derived fuel; said method comprising adding to said petroleum hydrocarbon or liquid biologically derived fuel at least one compound having formula (I),

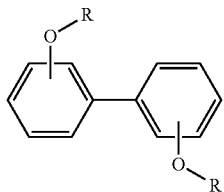

(I)

wherein R represents $C_4$-$C_{16}$ alkyl or $C_4$-$C_{16}$ alkenyl; and wherein each compound of formula (I) is present at a level from 0.01 ppm to 20 ppm.

2. A method for marking a petroleum hydrocarbon or a liquid biologically derived fuel; said method comprising adding to said petroleum hydrocarbon or liquid biologically derived fuel at least one compound having formula (I),

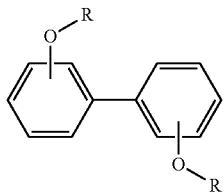

(I)

wherein R represents $C_1$-$C_{18}$ alkyl, $C_3$-$C_{18}$ alkenyl or $C_3$-$C_{18}$ alkenyl; each compound of formula (I) is present at a level from 0.01 ppm to 10 ppm and in which —OR groups are in 2,2'-positions on benzene rings in formula (I).

3. The method of claim 2 in which R represents $C_2$-$C_{18}$ alkyl or $C_3$-$C_{18}$ alkenyl.

4. The method of claim 3 in which R represents $C_3$-$C_{16}$ alkyl or $C_3$-$C_{16}$ alkenyl.

5. The method of claim 4 further comprising detecting the compounds of formula (I) by mass spectral analysis.

6. The method of claim 5 in which R represents $C_4$-$C_{16}$ alkyl.

7. The method of claim 6 in which said petroleum hydrocarbon or liquid biologically derived fuel is a petroleum hydrocarbon, biodiesel fuel or ethanol fuel.

* * * * *